United States Patent
Jung et al.

(10) Patent No.: US 10,540,324 B2
(45) Date of Patent: Jan. 21, 2020

(54) HUMAN HAPLOTYPING SYSTEM AND METHOD

(71) Applicant: SYNTEKABIO CO., LTD., Daejeon (KR)

(72) Inventors: Jongsun Jung, Daejeon (KR); Sunho Lee, Seoul (KR); Sojeong Ka, Seoul (KR); Jonghui Hong, Seoul (KR); Yangrae Cho, Cheongju-si (KR)

(73) Assignee: SYNTEKABIO CO., LTD., Daejeon (KR)

( * ) Notice: Subject to any disclaimer, the term of this patent is extended or adjusted under 35 U.S.C. 154(b) by 0 days.

(21) Appl. No.: 16/243,287

(22) Filed: Jan. 9, 2019

(65) Prior Publication Data

US 2019/0130996 A1 May 2, 2019

Related U.S. Application Data

(63) Continuation of application No. PCT/KR2016/015428, filed on Dec. 28, 2016.

(30) Foreign Application Priority Data

Jul. 29, 2016 (KR) .................. 10-2016-0096996

(51) Int. Cl.
*G06F 16/14* (2019.01)
*G06F 16/2457* (2019.01)
*G16B 20/20* (2019.01)

(52) U.S. Cl.
CPC ...... *G06F 16/148* (2019.01); *G06F 16/24578* (2019.01); *G16B 20/20* (2019.02)

(58) Field of Classification Search
CPC ................................................ G16B 20/20
See application file for complete search history.

(56) References Cited

U.S. PATENT DOCUMENTS

| 10,162,933 B2 * | 12/2018 | Bai ............. C12Q 1/6881 |
| 2004/0210400 A1 * | 10/2004 | Konvicka ......... G16B 40/00 |
| | | 702/20 |
| 2005/0089904 A1 * | 4/2005 | Beaulieu .......... C12Q 1/6827 |
| | | 435/6.11 |
| 2008/0241823 A1 * | 10/2008 | Gut ............... C12Q 1/6827 |
| | | 435/6.11 |

(Continued)

FOREIGN PATENT DOCUMENTS

| KR | 10-0834574 B1 | 6/2008 |
| KR | 10-0880531 B1 | 1/2009 |

(Continued)

OTHER PUBLICATIONS

International Search Report for PCT/KR2016/015428 dated Mar. 13, 2017 from Korean Intellectual Property Office.

(Continued)

*Primary Examiner* — Christopher J Raab
(74) *Attorney, Agent, or Firm* — Paratus Law Group, PLLC

(57) ABSTRACT

Disclosed is a human haplotyping method. The method includes: collecting a sequence of a gene to be analyzed; matching and aligning reads of the collected sequence to a reference stored in a database; electing candidate alleles from among alleles of the reference; and selecting a final allele from among the candidate alleles.

17 Claims, 7 Drawing Sheets

Specification includes a Sequence Listing.

(56) References Cited

U.S. PATENT DOCUMENTS

| | | | |
|---|---|---|---|
| 2014/0045706 A1 | 2/2014 | Fan et al. | |
| 2016/0125128 A1* | 5/2016 | Yang | G06N 5/04 706/46 |
| 2016/0132631 A1* | 5/2016 | Bremel | A61K 39/098 424/190.1 |
| 2019/0087540 A1* | 3/2019 | Jung | G16B 20/00 |

FOREIGN PATENT DOCUMENTS

| | | |
|---|---|---|
| KR | 10-2009-0105921 A | 10/2009 |
| KR | 10-0936238 B1 | 1/2010 |
| KR | 10-0956637 B1 | 5/2010 |
| KR | 10-0996443 B1 | 11/2010 |
| KR | 10-1010219 B1 | 1/2011 |
| KR | 10-1035959 B1 | 5/2011 |
| KR | 10-1117603 B1 | 3/2012 |
| KR | 10-1400717 B1 | 5/2014 |
| KR | 10-2014-0077769 A | 6/2014 |
| KR | 10-2014-0092135 A | 7/2014 |
| KR | 10-2014-0093408 A | 7/2014 |
| KR | 10-1460520 B1 | 11/2014 |
| KR | 10-2015-0024232 A | 3/2015 |
| KR | 10-1542529 B1 | 8/2015 |
| KR | 10-1693504 B1 | 1/2017 |
| KR | 10-1693510 B1 | 1/2017 |
| KR | 10-1693717 B1 | 1/2017 |
| KR | 10-1815529 B1 | 1/2018 |
| KR | 10-2018-0069651 A | 6/2018 |

OTHER PUBLICATIONS

Bai et al., "Inference of High Resolution HLA Types using Genome-wide RNA or DNA Sequencing Reads", BMC Genomics, Article No. 325, 2014, internal pp. 1-16, vol. 15.

Nariai et al., "HLA-VBSeq: Accurate HLA Typing at Full Resolution from Whole-genome Sequencing Data", BMC Genomics, Supplement 2, Article No. S7, 2015, internal pp. 1-6, vol. 16.

Huang et al., "HLAreporter: A Tool for HLA Typing from Next Generation Sequencing Data", Genome Medicine, Article No. 25, 2015, internal pp. 1-12, vol. 7.

Erlich et al., "Next-generation sequencing for HLA typing of class I loci", BMC Genomics, Article No. 42, 2011, internal pp. 1-13, vol. 12.

Liu et al., "ATHLATES: accurate typing of human leukocyte antigen through exome sequencing", Nucleic Acids Research, Article No. 14, 2013, internal pp. 1-8, vol. 41.

Warren et al. "Derivation of HLA types from shotgun sequence datasets", Genome Medicine, Article No. 95, 2012, internal pp. 1-8, vol. 4.

Bakker et al., "A high resolution HLA and SNP haplotype map for disease association studies in the extended human MHC", Nature Genetics Author manuscript, Apr. 17, 2009, internal pp. 1-16.

\* cited by examiner

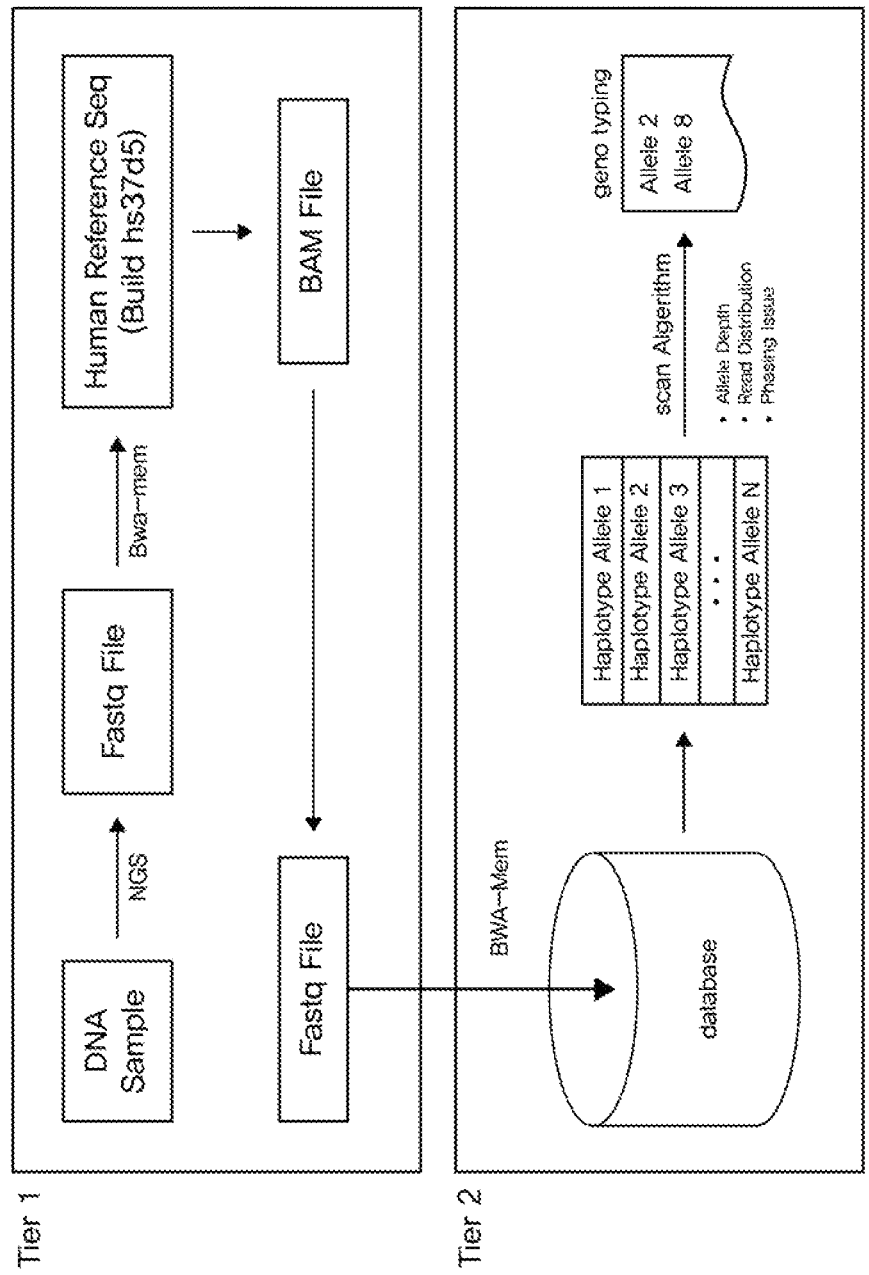

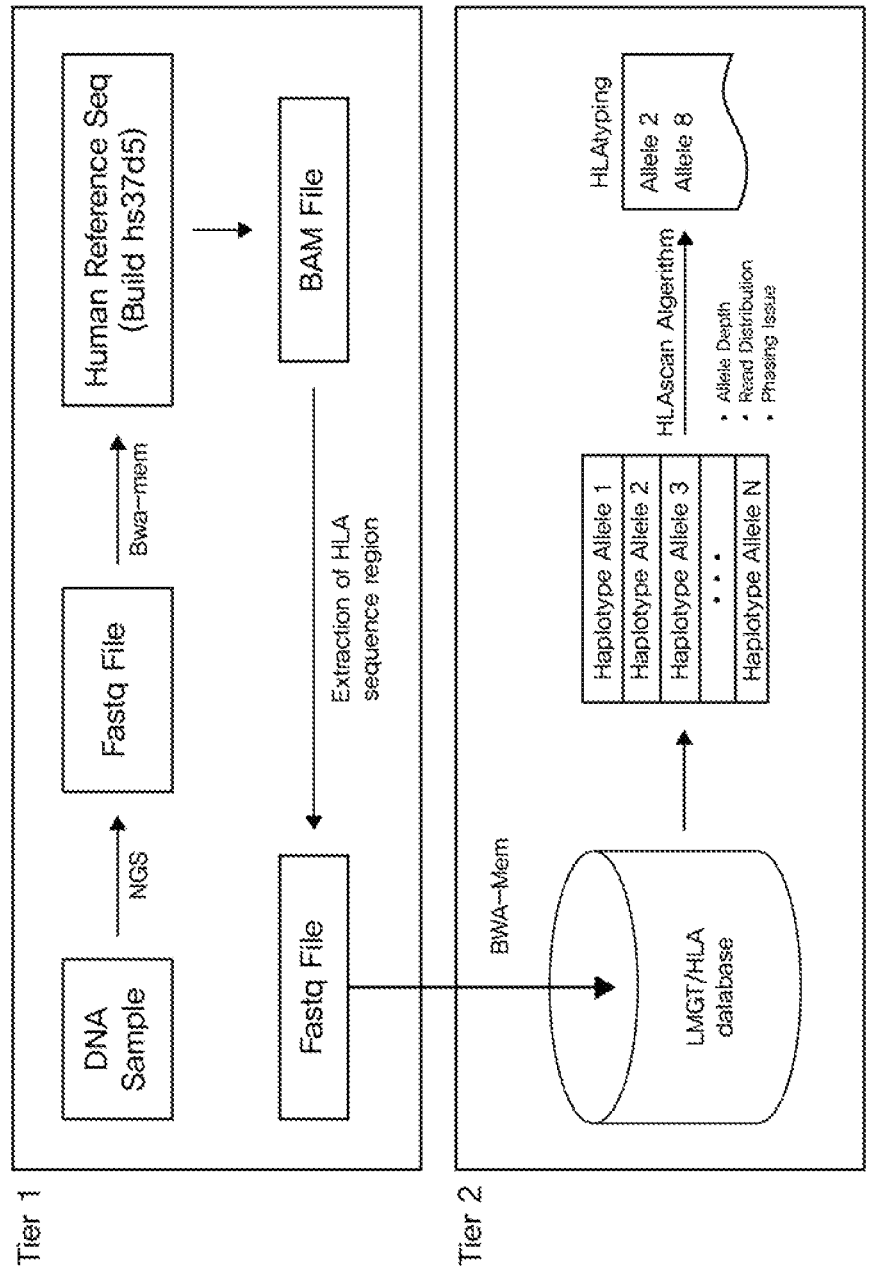
[Figure 2]

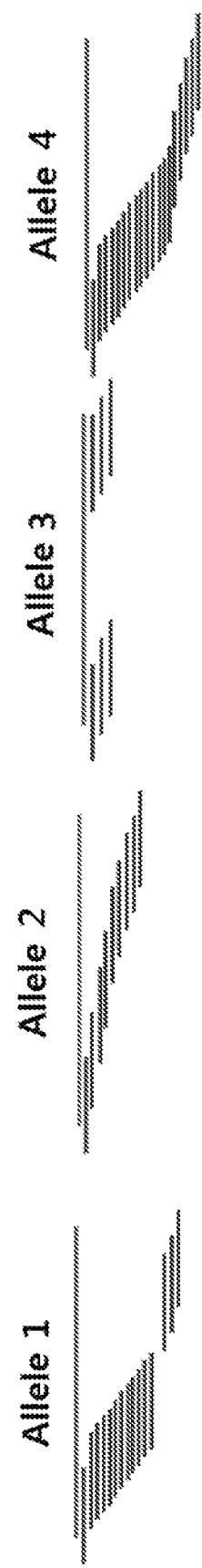
[Figure 3]

[Figure 4]

z : phased allele

...a............c..    x   ...a............t..   y   ...g............c..

Count a unique read for each allele x=3, y=2, z=0

[Figure 5]

02:01:01:01 (exome 3)

GCCACTCCACGGTGATGGGGCTCTGGAGGCTGGGGTGCTCCACGTGGCCAGGTGTAGACGTCTCCA

CGCTGGGGAGTCATTTCCAGCATCACCAGGATCTGGAAGGTCCAGTCACCATTCCTAATAAGGGG

GGTGGACACAACGCCAGCTGTCTCCCTCCTGGTCATTCCGAAACCACCGGACTTTGATCTGGGCTGG

ATAGAAATCTGTCACCGAGCAGACCAGCAGGTTGTGGTGGTTGAGGGCCTCTGTCCTGGATGGGGA

GATGGTCACTGTGGGCTCCA

02:02:01:01 (exome 3)

GCCACTCCACGGTGATGGGGCTCTGGAGGCTGGGGTGCTCCACGTGGCCAGGTGTAGACGTCTCCAC

GCTGGGGAGTCATTCCAGCATCACCAGGATCTGGAAGGTCCAGTCACCATTCCTAATAAGGGGGG

TGGACACAACGCCAGCTGTCTCCCTCCTGGCCATTCCGAAACCACCGGACTTTGATCTGGGCTGGATA

GAAATCTGTCACGAGCAGACCAGCAGGTTGTGGTGGTTGAGGGCCTCTGTCCTGGATGGGAGATG

GTCACTGTGGGCTCCA

[Figure 6]
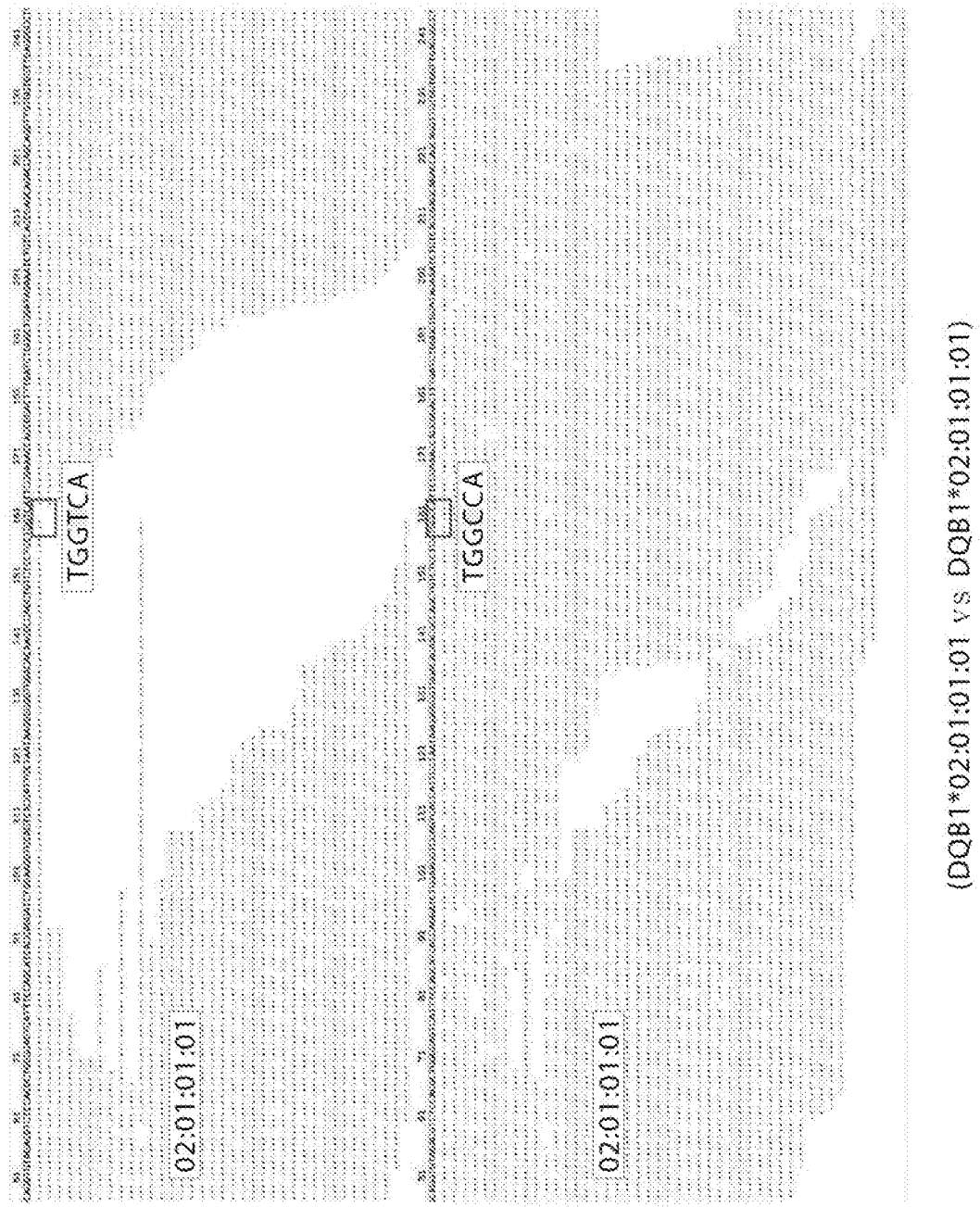

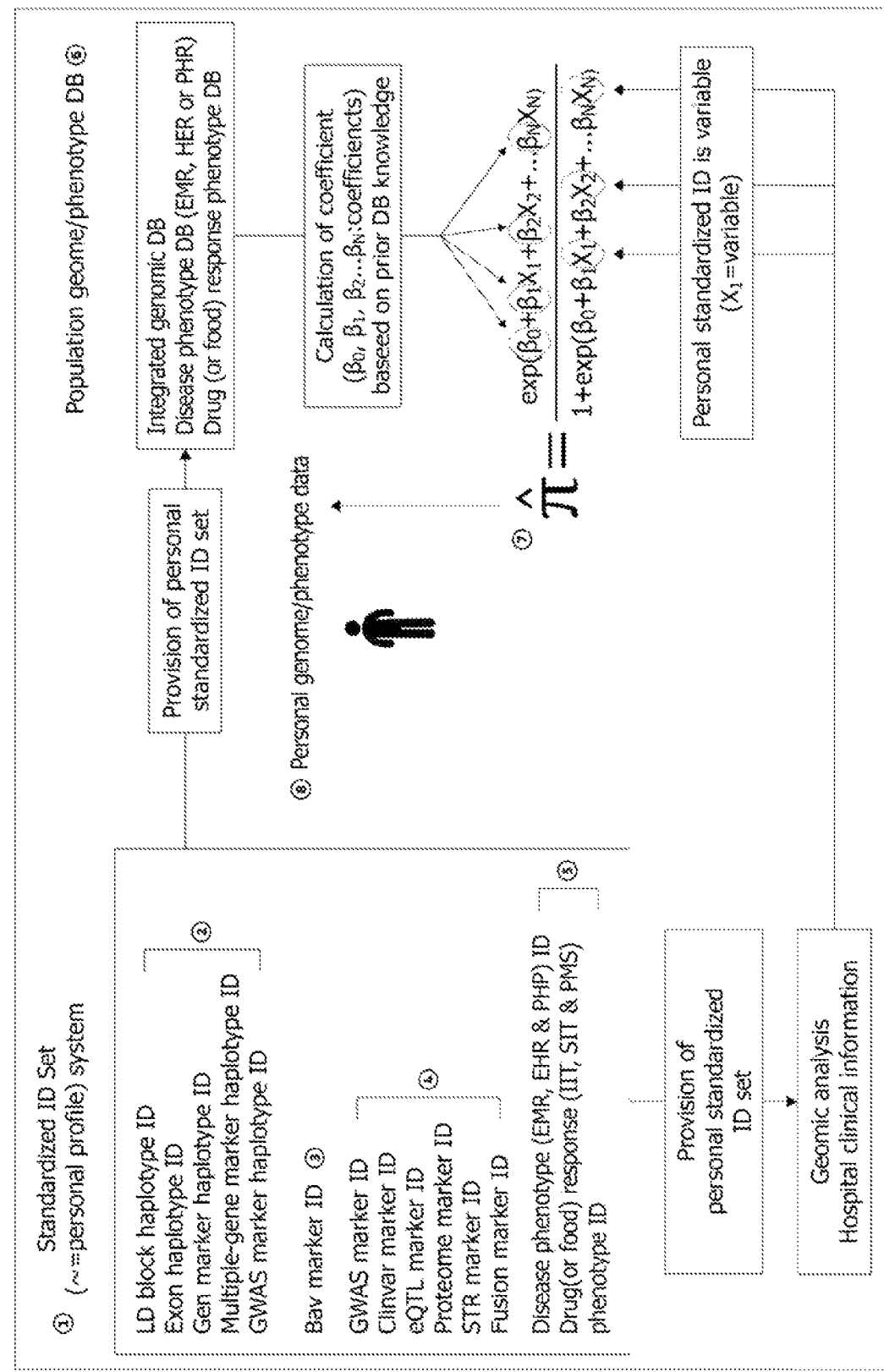

HUMAN HAPLOTYPING SYSTEM AND METHOD

CROSS-REFERENCE TO PRIOR APPLICATIONS

This application is a Continuation Application of PCT International Patent Application No. PCT/KR2016/015428 (filed on Dec. 28, 2016), which claims priority to Korean Patent Application No. 10-2016-0096996 (filed on Jul. 29, 2016), which are all hereby incorporated by reference in their entirety.

TECHNICAL FIELD

The present invention relates to a human haplotyping system and method which have increased accuracy and efficiency in detecting genotypes for identifying human genetic traits through a computerized system.

BACKGROUND ART

The current IT market trends are changing in the order of Google, Facebook, Amazon, cloud computing and Ubiquitous, and at the same time, biomedical, bioinformatics and genomics are also changing according to new trends in the order of bio-Google, system bio, personalized medicine and precision medicine. Particularly, in the Post-Human Genome Project era, the next generation sequencing technology has been developed rapidly and efforts have been actively made to realize individualized/personalized medicine.

Currently, the next generation sequencing technology is known to take about one week to sequence (decode) and analyze the entire genome of a person (x30). In addition, it was reported that about 100,000 next-generation sequencers were supplied worldwide, and it was that a significant amount of money has been invested in major companies which have developed the third-generation sequencer (Ion Torrent: 2.5 generation; Pacific BioScience: third generation).

In addition, this field is the fastest advancing and developing field among all businesses in the world. As this trend progresses, the cost for sequencing and analyzing the entire genome of a person is expected to decrease to less than approximately $1,000 within the next two to three years. The most useful and immediately practicable technologies based on the above next generation technologies are clinical genomics, pharmaco-genomics and translational medicine. In addition, such clinical genomics has recently been applied to medical genomics, and such medical genomics, along with patient stratification technologies, have created a new discipline and new language called Precision Medicine mentioned by U.S. President Obama.

As described above, information on genetic variation is increasing every year, and the area of analysis accuracy will be continuously expanded by expansion of verified data according to the present invention.

Meanwhile, the applicant has continued to develop technology in order to improve the technical requirements of the above-mentioned genetic analysis field.

As a result of these efforts, the applicant has developed methods for precision medicine, clinical information, proteome and genome information related to bio-big data, and construction of analysis systems for increasing the analysis speed thereof. In particular, the applicant developed a GPU (graphic process unit)-based analysis system for analysis speed (Korean Patent No. 10-0996443), and developed information searching methods based on characteristic files of an RVR (records virtual rack) analysis tool which is a technique for increasing data comparison speed (Korean Patent Nos. 10-0880531, 10-1035959 and 10-1117603).

In addition, the applicant applied RVR and GPU (graphic process unit) to proteomes (Korean Patent No. 10-1400717), and developed allele depth-based ADISCAN analysis tools for efficiently determining variant calling and the level of rare variation between a control and an individual genome (Korean Patent No. 10-1460520, 10-1542529 and 10-2014-0020738).

In addition, the applicant developed methods for construction of an integrated genome DB for efficiently managing genome information, identification of mutations for disease causes, and genotype calculation for patient stratification (Korean Patent Nos. 10-2015-0187554, 10-2015-0187556 and 10-2015-0187559), and a method for computing human haplotyping from genome information (Korean Patent Application No. 10-2016-0096996).

In addition, using middleware specialized for storage of big data such as integrated genetic DB, MAHA supercomputing systems were developed which enables thousands of genomic bulk data to be analyzed simultaneously in a parallel distributed environment developed by the Electronics and Telecommunications Research Institute (ETRI) (Korean Patent Nos. 10-1460520, 10-1010219, 10-0956637, 10-093623, 10-2013-0005685, 10-2012-0146892 and 10-2013-0004519).

Using the MAHA system provided from the Electronics and Telecommunications Research Institute, the applicant has developed the first domestic supercomputing system, which has an optimized environment utilizing bio big data for clinical applications and is integrated with an integrated genome analysis system for precision medicine implementation.

In particular, although MAHA-Fs (a storage system for ultrahigh speed I/O for bulk data such as genome) was tailored to a common cloud computing environment, the applicant has developed MAHA-FsDx, which can be used for diagnosis in a clinical environment, that is, a hospital, by clearly defining reproducibility, precision and system limitations. In addition, Prior Art Documents (001) to (019) summarize the technical elements for a personal genome map-based personalized medical analysis platform.

NPs that account for more than 0.1% of the human genome sequence have been the subjects for correlating human phenotypic variations. Accordingly, various platforms for performing haplotyping in an accurate and rapid manner have been studied.

Here, the haplotyping may also be performed on the entire human genome, but currently, it is generally performed on specific SNP regions for promptness and accuracy of typing.

This is because the accuracy of haplotyping results increases as more human genome references are secured, but so far, references have been secured so that reliability can be ensured only for a reference of a specific SNP region.

The haplotyping may be performed on various SNP regions, but in recent years, it has been most actively used in the field of HLA typing for human leukocyte antigen genes.

Meanwhile, a general haplotyping process is schematically shown in FIG. 1. As shown therein, a BAM filed is generated from a DNA sample to be analyzed, and a specific region to be analyzed is extracted therefrom, thereby generating a Fastq format file.

Next, the Fastq format file is compared with haplotype allele references stored in a database, and the genotype of the DNA to be analyzed is read.

This haplotyping technology is also applied to HLA typing in which a specific region is limited to HLA gene.

Methods and technologies, which have recently studied on the HLA typing, are disclosed below.

However, the prior art as described above has the following problems.

That is, haplotyping according to the prior art has a problem that it is difficult to obtain accurate test results, because of the high polymorphism, linkage disequilibrium and sequence similarity of human genes.

In order to overcome this problem occurring when the prior art is used, the length of sequence reads should be increased. In this case, however, there are problems in that the analysis time increases and the analysis process becomes complicated, resulting in a decrease in analysis efficiency.

LIST OF PRIOR ART PATENT DOCUMENTS (Patent document 1) (001) Korean Patent No. 10-0880531;
(Patent document 2) (002) Korean Patent No. 10-0996443;
(Patent document 3) (003) Korean Patent No. 10-1035959;
(Patent document 4) (004) Korean Patent No. 10-1117603;
(Patent document 5) (005) Korean Patent No. 10-1400717;
(Patent document 6) (006) Korean Patent No. 10-1460520;
(Patent document 7) (007) Korean Patent No. 10-1542529;
(Patent document 8) (008) Korean Patent Application No. 10-2015-0187554;
(Patent document 9) (009) Korean Patent Application No. 10-2015-0187556;
(Patent document 10) (010) Korean Patent Application No. 10-2015-0187559;
(Patent document 11) (011) Korean Patent Application No. 10-2016-0096996;
(Patent document 12) (012) Korean Patent No. 10-0834574;
(Patent document 13) (013) Korean Patent No. 10-1010219;
(Patent document 14) (014) Korean Patent No. 10-0956637;
(Patent document 15) (015) Korean Patent No. 10-0936238;
(Patent document 16) (016) Korean Patent Application No. 10-2013-0005685;
(Patent document 17) (017) Korean Patent Application No. 10-2012-0146892;
(Patent document 18) (018) Korean Patent Application No. 10-2013-0004519;
(Patent document 19) (019) Korean Patent Application No. 10-2016-0172053.

DISCLOSURE

Technical Problem

The present invention has been made in order to the problems occurring in the prior art, and the present invention is intended to solve problems associated with reduced haplotyping accuracy, which is due to the high polymorphism and sequence similarity, by use of short sequence reads generated from an existing illumine system.

Specifically, the present invention is intended to provide a haplotyping method and system which perform haplotyping with increased accuracy by use of short sequence reads based on an alignment based approach).

Technical Solution

A system for computing the cause of disease and drug (or food) response calculates multiple regression analysis coefficients based on population genetic information and clinical information, and calculates a relationship index (pi, $\pi$), which is the result of logistic regression, by use of personal genetic information and clinical information as variables. In this regard, the relationship index (pi, $\pi$) is calculated by receiving a standardized ID set based on personal genome information (genotype marker ID) and hospital clinical information (a specific genotype or various genotypes) and using the values as input. In addition, when the relationship index (pi, $\pi$) is in the range of 0.7 to 1, the specific genetic marker ID of the person becomes the direct (or indirect) cause of a given phenotype.

As shown in FIG. 7, the standardized ID set system uses the term "genotype (trait) calculation". Although scientists may have different opinions, the definition of genotype (trait) in this patent is determined by a standardized ID set and similar methods.

Namely, the standardized ID set refers to haplotyping-based LD block haplotype ID, Exon haplotype ID, gene marker haplotype ID, multiple gene marker haplotype ID, GWAS marker haplotype ID, BAV marker ID of physiologically active single variations or sets in this patent, and ID in markers in a common independent (or individual) biomarker DB, and it includes GWAS markers, Clinvar markers, eQTL markers, proteome markers, STR markers, Fusion markers, and the like.

In addition, it includes diagnostic phenotype information such as electronic medical records (EMRs), electronic health records (EHRs) and personal health records (PHRs), etc., held by hospitals or medical examination centers.

In addition, it includes drug clinical phenotype information such as drug responders/non-responders of drug and health food (or food) clinical (IIT: investigator initiative clinical trial, SIT: sponsor initiative clinical trial, PMS: post-market survey).

In addition, it refers to a database for calculating coefficient values using the integrated genomic DB and the standard phenotype disease information included in hospital medical systems. Here, different multiple coefficient values per phenotype are calculated, and if necessary, multiple coefficient values for multiple phenotypes may be calculated.

Finally, as information on personal genome and hospital phenotypes is given, the relationship index (pi, $\pi$) which is the result of multiple logistic regression is obtained.

Here, the relationship index ($\pi$) is given as a probability score from 0 to 1. A relationship index close to 0.7-1 indicates that a probability of having a given phenotype is high, and a relationship index of 0-0.3 is opposite to a given phenotype. In addition, a relationship index of 0.4-0.6 indicates that the phenotype is in an intermediate stage.

In particular, haplotyping-based haplotypes include LD (linkage disequilibrium) block haplotypes, Exon haplotypes, gene marker haplotypes, multiple gene marker haplotypes, and GWAS (genome wide association study) marker haplotypes. For common points in haplotypes, haplotyping of specific units of human genes is performed, and among them, only important markers (e.g., GWAS markers) may be used, or the whole sequence (exon, gene, or LD block) may be used. The haplotype ID generated as described above may be named genotype (trait) which is a generic term. In particular, haplotyping-based haplotypes may also be used as human standardized ID sets.

Meanwhile, the present invention comprises: a sequence read collection step of collecting the sequence of a gene to be analyzed; a sequence read alignment step of matching and aligning the collected sequence reads with a reference stored in a database; an allele selection step of selecting candidate alleles from among alleles of the reference; and an allele determination step of selecting a final allele from among the candidate alleles.

Herein, the sequence real collection step may also comprise selecting and collecting a sequence read of a specific region.

The specific region may be an HLA gene region.

The database may be an IMGT/HLA DB.

The sequence read alignment step may comprise: a step of aligning the sequence leads to the reference stored in the database; and filtering the aligned sequence reads depending on the absolute value of matching with the reference alleles.

Furthermore, the selection of the alleles may be performed by selecting the candidate alleles depending on the distribution of the aligned sequence reads (the distribution of read alignments as a tiling array pattern).

Meanwhile, determination of the distribution of the aligned sequence reads may comprise determining that alleles of the reference are false alleles when the dispersion of the distribution of the aligned reads on the reference is low.

In addition, determination of the distribution of the aligned sequence reads may comprise converting the distribution of the aligned reads into a score, and determining that the alleles are false allele when the score is lower than a threshold value.

Here, the score may be calculated by the following equation:

$$score = \sum_{j=1}^{m} \left( \frac{|noreadj|}{c} \right)^4$$

wherein m is a value determined depending on the length of alleles; C is a constant; and noread is a constant determined for a region to which sequence reads are not aligned.

In addition, the allele gene determination step is performed by a unique read algorithm, in which the unique read algorithm may be configured such that when 4 or more candidate alleles are present on the reference, the algorithm excludes candidate alleles other than alleles, which 100% match with the sequence reads (mapping with 100% match), from the 4 or more candidate alleles.

In addition, the allele determination step is performed by a unique read algorithm, in which the unique read algorithm may be configured such that when 3 or less candidate alleles are present on the reference, the algorithm counts the number of unique reads which are sequence reads aligned to only any one of the candidate alleles, and the algorithm selects two final candidate alleles depending on the number of the unique reads.

In addition, the unique read algorithm may be configured such that when the two final candidate alleles include different unique reads, the algorithm determines the alleles as heterozygous alleles.

In addition, the unique read algorithm may be configured such that when any one of the two final candidate alleles includes unique reads, the algorithm determines the alleles as homozygous alleles.

Meanwhile, the present invention includes a human haplotyping system that performs the human haplotyping method by matching and aligning sequence reads, collected from a gene to be analyzed, to reference alleles stored in a database, selecting candidate alleles from among the reference alleles, and selecting two final alleles from among the candidate alleles, wherein the aligning of the sequence reads is performed by aligning the sequence reads to the reference stored in the database, and then filtering the aligned sequence reads depending on the absolute value of matching with the reference alleles.

Advantageous Effects

The haplotyping system and method according to the present invention as descried above can exhibit the following effects.

Namely, according to the present invention, while haplotyping is performed using short sequence reads based on an alignment based approach, the efficiency of selection of candidate alleles can be increased by use of a function of converting the distribution of aligned sequence reads into a score.

In addition, according to the present invention, false alleles caused by phase issues can be detected and removed by use of a unique read algorithm, thereby providing human haplotyping results with increased accuracy.

DESCRIPTION OF DRAWINGS

FIG. 1 illustrates an overall process of performing haplotyping according to the present invention.

FIG. 2 illustrates an overall process of performing haplotyping according to a specific embodiment of the present invention.

FIG. 3 illustrates an example of selecting candidate alleles depending on the distribution of aligned sequence reads according to a specific embodiment of the present invention.

FIG. 4 illustrates an example of selecting final candidate alleles by a unique read algorithm according to a specific embodiment of the present invention.

FIG. 5 illustrates an example of a false allele to describe a specific embodiment of the present invention.

FIG. 6 illustrates another example of a false allele to describe a specific embodiment of the present invention.

FIG. 7 is a conceptual view showing the conceptual configuration of a system for identifying the cause of disease and drug response according to the present invention.

BEST MODE

The human haplotyping method according to the present invention as described above comprises: a sequence read collection step of collecting the sequence of a gene to be analyzed; a sequence read alignment step of matching and aligning the collected sequence reads with a reference stored in a database; an allele selection step of selecting candidate alleles from among alleles of the reference; and an allele determination step of selecting a final allele from among the candidate alleles.

Herein, the sequence real collection step may also comprise selecting and collecting sequence reads of a HLA gene region, and the database is an IMGT/HLA DB.

Furthermore, the sequence read alignment step may comprise: a step of aligning the sequence leads to the reference stored in the database; and filtering the aligned sequence reads depending on the absolute value of matching with the reference alleles.

Furthermore, the selection of the alleles is performed by selecting the candidate alleles depending on the distribution of the aligned sequence reads (the distribution of read alignments).

In addition, determination of the distribution of the aligned sequence reads preferably comprises converting the distribution of the aligned reads into a score, and determining that the alleles are false allele when the score is lower than a reference value. Here, the score is calculated by the following equation:

$$score = \sum_{j=1}^{m} \left( \frac{|noreadj|}{c} \right)^4$$

wherein m is a value determined depending on the length of alleles; C is a constant; noread may be a constant determined for a region in which sequence reads are not aligned.

In addition, the allele determination step is preferably performed by a unique read algorithm, in which the unique read algorithm may be configured such that when 3 or less candidate alleles present on the reference, the number of unique reads which are sequence reads aligned to only any one of the candidate alleles is counted, and two final candidate alleles are selected depending on the number of the unique reads.

MODE FOR INVENTION

Hereinafter, a human haplotyping system and method according to a specific embodiment of the present invention will be described with reference to the accompanying drawings.

The human haplotyping system and method according to the present invention may be applied to haplotyping of the entire human genome and may also be applied to specific SNP regions.

Here, "specific regions" refers to gene (or a combination of genes) regions involved in specific functions, and may typically include HLA gene regions responsible for regulation of the human immune system, DMET gene regions responsible for drug metabolism-related function, KIR gene regions involved in immune cell expression, and ABO gene regions related to blood characteristics.

Thus, the present invention may be applied not only to haplotyping of the entire human genome, but also to haplotyping of specific regions, such as HLA typing, DMET typing, KIR typing, ABO typing and Cytokine Gene typing or the like.

Here, DMET (Drug Metabolizing Enzymes and Transporters) refers to enzymes and transporters, which are involved in drug absorption and disposition and drug activity.

For example, DMET includes cytochrome p450 enzyme family (CYPs), uptake transporters, efflux transporters, and the like. One family includes several genes, and the gene sequences thereof are similar to each other and at the same time, polymorphic.

The difference in DMET gene sequence between individuals may influence drug responses, side effects, disease susceptibility and the like and may also become a criterion for selection of proper drugs. Thus, DMET typing is a research field that recently received attention in pharmacogenetics.

In addition, KIRs (Killer-cell Immunoglobulin-like Receptors) are proteins which are displayed on the surface of specific immune cells such as natural killer (NK) cells or T cells.

KIRs regulate the cell killing ability of NK cells and T cells by interaction with major histocompatibility (MHC) class I on the surface of other cells.

Thus, this function of KIRs is associated with susceptibility and response to infection, autoimmune diseases, cancer and the like.

In addition, the KIRs are highly polymorphic, and thus the gene sequence thereof significantly differs between individuals, and the level or kind thereof differs between individuals.

Meanwhile, ABO (blood type) is a gene that plays a major role in the relationship between ABO blood type and blood transfusion. It is located at chromosome 9q34 and can be divided into three alleles (A, B and O types) by a conventional serum technique.

There is also subgroups in alleles of each of A, B and O. In rare cases, a problem may arise in that blood transfusion between the subgroups is impossible, even in the case of even the same blood type.

Cytokines, chemokines, growth factors, and hormones share many similarities and act as essential biochemical messengers for housekeeping functions, as well as, having crucial roles in pathological and stem-cell related growth and regulation. Their allele frequencies are significantly different in many other populations.

In addition, it is possible to apply the same logic to all human genes (40,000 genes) for calculation.

Hereinafter, HLA typing will be described as a representative example in order to explain the present invention in detail.

The major histocompatibility complex regions are the most complex areas of the human genome and are responsible for the regulation of the human immune system. Among them, the human leukocyte antigens (HLAs) genes are present in about 3 Mbp stretch of chromosome 6 and play a major role in the adaptive immune response that suppresses and eliminates pathogens.

From a clinical point of view, the risk of rejection in organ transplantation can be reduced when the HLA genes are similar between a donor and a recipient. Therefore, accurate HLA typing is a very important issue.

However, accurate HLA typing is very difficult because of the high polymorphism, linkage disequilibrium and sequence similarity of the HLA genes.

For example, there are thousands of alleles reported in the IMGT/HLA database for exons 2-4 of HLA-A gene in class I, and the alleles are very similar between HLA-A, B and C genes. At low resolution (2-digits), the same antigen peptide by low resolution (2-digits) can cause an allogeneic response due to differences in amino acids. For this reason, HLA typing needs to be performed to high resolution (4-digits) at the amino acid level.

Conventional methods for high-resolution HLA typing include a polymerase chain reaction (PCR) by sequence specific oligonucleotide (SSO) and sequence-based typing (SET). However, such methods are performed depending on the worker's labor and thus low-throughput and high costs are problematic.

Meanwhile, a TAS (Targeted Amplicon Sequencing) approach shows relatively high throughput compared to the PCR method, and thus makes it possible to perform HLA typing with high accuracy by generating long reads with hundreds of bases at low costs.

However, because of efficiency and costs, most of the recent data generated are genome-wide sequences, whole genome sequences (WGS) or whole exome sequences (WES), and such data have short sequence reads (~101 bp)

rather than long reads. Therefore, there is a need to perform HLA typing with the same (or more) accuracy and economy as those of the TAS approach by using such short sequence reads.

That is, the HLA typing according to the present invention is to provide HLA typing with improved accuracy and efficiency by using short reads.

HLA typing methods using short sequence reads are broadly divided into two categories.

One method is to determine the overall HLA type by assembling short reads to generate long contigs, and another method comprises aligning all short sequence reads with reference to known allele sequences and then determining actual alleles using the aligned information.

In the assembly-based method that uses short reads, it is difficult to solve the problem associated with the determination of false positive alleles caused by a phasing issue, and the required time is also long.

Meanwhile, in the alignment-based method, it is not easy to determine actual alleles, because known alleles are very similar due to high polymorphism of the HLA gene region.

Despite these problems, with the great interest of researchers, HLA reporter was introduced as an assembly-based method, and PHLAT or the like was introduced as an alignment-based method. Recently published HLA reporter and PHLAT show accurate HLA typing results compared to previous HLA typing.

The HLA typing according to the present invention performs highly accurate HLA typing for genome-wide short sequencing data, which is hereinafter referred to as HLAscan.

In conventional arts such as PHLAT, candidate alleles were selected using aligned reads and depth coverage. However, HLAscan according to the present invention uses the distribution of reads aligned to alleles.

In addition, the present invention uses an algorithm for removing false positive alleles selected due to phase issues (this algorithm is hereinafter referred to as 'unique read algorithm').

A test was performed using HLAscan according to the present invention. As a result, the HLAscan showed highly increased accuracy for eleven 1000-genome samples, fifty-one HapMap samples, and five in-house samples, compared to a conventional art.

Hereinafter, the detailed configuration of HLAscan according to the present invention will be described.

HLAscan according to the present invention provides:

1) a score function considering the distribution of aligned reads in order to select candidate alleles; and 2) an unique read algorithm for detecting false positive alleles caused by phase issues.

HLAscan is fundamentally based on an alignment-based approach, and is largely divided into two steps as shown in FIG. 2.

In step 1 (Tier1), raw sequence reads generated from an NGS system are aligned to a whole-genome reference, thereby generating a binary alignment map (BAM), and then sequence reads corresponding to HLA gene regions are selected.

In step 2 (Tier2), the sequence reads are respectively aligned to all alleles present in an IMGT/HLA database. Taking HLA-A as an example, 3182 known alleles of the HLA-A gene are present in the IMGT/HLA database, and the HLAscan align the collected sequence reads with reference to these alleles.

Furthermore, using the aligned information, final alleles are determined.

To determine final alleles from the aligned information, the present invention provides a score function considering the distribution of aligned reads in order to select candidate allele, and provides a unique read algorithm in order to eliminate phase issues in selection of final alleles.

Hereinafter, description will be made of the detailed contents of the score function considering the distribution of aligned reads and the unique read algorithm, which are provided by HLAscan according to the present invention.

Score Function Considering the Distribution of Aligned Reads

HLAscan removes false alleles by use of the score function considering the distribution of aligned reads in order to select true alleles from among thousands (about 8,000) allele forms stored in the IMGT/HLA database.

Alleles left unremoved in this process are referred to as candidate alleles.

Here, the "score function considering the distribution of aligned reads" means that when the distribution of aligned reads on the reference is not uniform, alleles of the reference are determined to be false alleles.

For example, given read_i ($1 \leq i \leq n$) aligned to positions s_i to e_i of a reference sequence (ref), it is determined that read_i was aligned to position (s_i+e_i)/2 of the ref. In addition, the consecutive positions of the reference, to which reads are not aligned, are referred to as noread_j ($1 \leq j \leq m$).

In this case, the score function can be calculated by $$\text{score} = \sum_{j=1}^{m} \left( \frac{|noread j|}{c} \right)^4$$

(c is a constant).

When the calculated value for the reference is higher than a threshold value, the reference may be determined to be a reference for false alleles, and the alleles of the reference can be excluded from candidates.

Unique Read Algorithm

The unique read algorithm according to the present invention includes: 1) an algorithm that removes false positive candidate alleles when a plurality of candidate alleles are present; and 2) an algorithm that detects and removes candidate alleles, caused by phase issues, when three or less candidate alleles are present.

In addition, based on the determination results as described above, the unique read algorithm according to the present invention can determine whether the final alleles are homozygous or heterozygous.

For example, it is assumed that sequence reads are collected from the gene to be typed and there is no sequencing error.

When two reads A and B which have different sequences are mapped with 100% match to positions "x" to "y" of allele_p and allele_q ($1 \leq p$, $q \leq t$), respectively, among candidate allele_i ($1 \leq i \leq t$) which are t in number, and when the two reads are not mapped to other regions, the actual gene of the corresponding sample is a heterozygous gene that has one strand, comprising the sequence of read A, and one strand comprising the sequence of read B.

Thus, candidate alleles, to which any of read A and read B is not mapped with 100%, are false positive alleles, and thus removed.

In addition, when 3 or less candidate alleles are present, the unique read algorithm according to the present invention counts the number of sequence reads aligned to each of the candidate alleles and selects the first candidate allele and the second candidate allele in the order of the number of the sequence reads. In addition, it repeats the same process on the two selected candidate alleles.

When the two candidate alleles all have unique aligned reads, the two alleles are selected as final alleles. In this case, the final alleles are heterozygous. In addition, when only one candidate allele has unique aligned reads (when aligned reads in one allele includes all aligned reads of the other allele), only the allele having the unique aligned reads is output as a final result. In this case, the final allele is homozygous.

HLAscan Test According to the Present Invention

In a test according to the present invention, the following samples were used: 11 samples from the 1000 Genome projects, the whole exome sequencing (WES) of which was analyzed and published; 51 samples from the HapMap projects; and 5 internal Korean samples.

The test according to the present invention shows the predictions of HLAscan for HLA class I (HLA-A, HLA-B, and HLA-C) and class II (HLA-DRB1 and HLA-DQB1) regions (additional file: Table R12, R22, R32). To evaluate the performance of HLAscan, the predictions of HLAreporter[ref] and PHLAT[ref] are used as comparisons.

To avoid a comparison biased to HLAscan, each of methods evaluates accuracy according to the criteria presented in their paper. The results for eleven 1000-genome samples are shown in Table R1, the results for fifty-one HapMap samples are shown in Table R2, and five Korean samples are shown in Table R3.

1) Collection of Sequences of HLA Gene Regions

Since the majority of publicly generated data are whole-genome sequence (WGS) or whole exome sequences (WES), sequence reads generated from HLA gene regions are selected for HLA typing.

HLAscan aligns sequence reads to an hs37d5 WGS reference by use of bwa-mem v0.7.10-r789 and collects all sequence reads aligned to HLA-gene regions.

Since it is shown that sequence similarity is high between HLA genes and low in other region, sequence reads generated from those other than HLA genes can be simply removed.

HLAscan according to the present invention does not classify sequence reads by specific HLA genes in this process. However, conventional assemble-based methods such as HLAreporter and HLAminer, final haplotypes are determined from given short sequence reads by use of de novo assembly.

Thus, the accuracy of the selection of sequence reads for the HLA gene to be typed has a direct effect on the accuracy of HLA typing.

However, because of sequence similarity between HLA genes (e.g., HLA-A, HLA-B, and HLA-C), this process is not easy, and HLA reporter collects sequence reads of a specific HLA gene by use of an IMGT/HLA database.

In HLAscan according to the present invention, sequence reads of the HLA gene of interest are selected during an alignment process based on the IMGT/HLA database, and thus there is less need to select the correct sequence reads during the process.

That is, the HLAscan according to the present invention leaves only 100% matching sequence reads in the alignment of sequence reads to the IMGT/HLA database, and thus accuracy is not critical in selecting sequence reads of the gene of interest.

Namely, the reason why the HLAscan according to the present invention selects sequence reads of HLA gene regions is because of efficiency rather than accuracy.

Accordingly, sequence reads generated from a significant number of HLA genes regions can be removed by a very simple method, resulting in speed increases of several tens of times or more when aligning the collected sequence reads to thousands of alleles of the IMGT/HLA database.

This is because step 1 (Tier 1) of FIG. 2 can be omitted when target sequencing for HLA-gene regions is performed.

2) Reads Alignment

The HLAscan aligns sequence reads, target-sequenced for selected HLA gene regions, to all reference alleles, respectively, which are present in the IMGT/HLA database, by use of bwa-mem v0.7.10-r789 in a default option.

Because of the sequence similarity between HLA genes and the existence of large number of alleles for most HLA genes, the HLAscan maps only reads which 100% match with reference alleles, thereby increasing the accuracy of read alignment.

However, despite these strong limitations, sequence reads generated from other genes can be mapped to alleles of the gene of interest.

3) Selection of Candidate Alleles

In order to select candidate alleles, PHLAT and Major (2013') which are conventional arts show a simple but accurate HLA typing method considering reads alignment and depth coverage.

However, the HLAscan according to the present invention selects candidate alleles in view of the distribution of read alignments for more accurate HLA typing.

As can be seen in FIG. 3, the appearance of reads aligned to four alleles can be seen. Alleles 2 and 4 are alleles of an actual sample, and allele 1 is a phased allele caused by the binding of the anterior part of allele 4 to the rear part of allele 2. Allele 3 is an allele having a considerable portion whose sequence differs from those of actual alleles 2 and 4.

When 'reads' are taken into consideration according to the conventional art PHLAT, allele 4 and allele 1 are evidently selected, and actual allele 2 cannot be selected due to phased allele 1. Even when depth coverage is taken into consideration, allele 4 is evidently selected, but it is impossible to select one of allele 1 and allele 2.

Meanwhile, because the score function takes into consideration the degree to which the aligned reads are evenly distributed, the HLAscan according to the present invention can clearly select allele 2 from among allele 2 and allele 4.

The HLAscan according to the present invention calculates a score for each allele by use of the score function, and removes alleles having a score higher than a specific value. The constant value used in the score function is 30, and the cutoff score is 200.

Here, the score is 0 or more, and the smaller the score, the better it is.

In other words, among non-removed alleles, alleles that show completely the same distribution of reads are grouped into one group.

Thus, reducing the number of candidate alleles helps to increase the accuracy of the determination of final alleles as described below.

4) Determination of Final Alleles Considering Phase Issue

A phase issue is a linkage disequilibrium region and becomes a serious problem when data of short sequencing reads are used.

The present invention proposes an efficient algorithm to solve such a problem. In the experimental range actually performed by this algorithm, it can be seen that the phasing problem was solved.

That is, the algorithm according to the present invention uses information on the number of unique aligned reads for each candidate allele and effectively solves the phase issue.

In particular, when the number of candidate alleles is 3 or less, the algorithm according to the present invention detects a phased allele very accurately.

In an example shown in FIG. 4, x and y are actual alleles, and z is a phased allele generated from x and y. Among aligned reads, reads aligned to all x, y, and z are green; reads aligned to x and z are blue; reads aligned to y and z are purple; and reads uniquely aligned to only one allele are gray.

The HLAscan algorithm according to the present invention determines x and y with 3 and 2 unique aligned reads as final candidate alleles, and discards z having no unique aligned read.

Because HLA genes have a large number of alleles and a very similar sequence between alleles and have sequences which similar between the alleles, t is not easy to determine whether the genes are homozygous haplotypes or heterozygous haplotypes.

However, according to the present invention, when two final candidate alleles are given and when reads aligned to allele B of the two candidate alleles include all reads aligned to allele A, allele A is removed.

Meanwhile, when the two alleles all have unique aligned reads, they are determined to be heterozygous.

Results of HLAscan Test According to the Present Invention

1) Predictions of 11 Samples from 1000 Genome Projects

To verify the accuracy of the HLAscan, predictions of 11 samples from 1000 genome projects, subjected to conventional laboratory HLA-typing [Liu et al.], were performed. Predictions of HLAreporter for the 11 samples [HLAreporter] and predictions of PHLAT for 10 overlapping samples [PHLAT] were used as comparisons.

PHLAT and HLAreporter, used as conventional comparative technologies, were reported to have higher accuracy than other conventional technologies.

Five genes (HLA-A, B, C, DRB1, and DQB1) for each of 11 samples, and two alleles for each of the genes are selected, and predictions are performed for a total of 110 alleles.

For predictions of homozygous alleles, two alleles are judged as predicted alleles.

In PHLAT, predictions for 100 alleles were performed. The results of predictions for each method are shown in additional file: Table R2.

As shown in Table 1, HLAscan and HLAreporter showed 100% accuracy for predictions of 110 alleles, whereas PHLAT showed relatively low accuracy (three 2-digits mistyped (97%), two 4-digits mistyped (95%)) for predictions of 100 alleles. In addition, in HLAreporter, there were 13 cases in which a number of alleles were reported due to ambiguity for phases, but these cases were not judged as mistyped.

TABLE 1

| Methods | # of examined alleles | Phase | Wrong (2-digits) | Wrong (4-digits) | Accuracy (2-digits wrong) | Accuracy (4-digits wrong) |
| --- | --- | --- | --- | --- | --- | --- |
| HLAreporter | 110 | 13 | 0 | 0 | 100% | 100% |
| PHLAT | 100 | — | 3 | 2 | 97% | 95% |
| HLAscan | 110 | — | 0 | 0 | 100% | 100% |

<Table 1. Accuracies (Liu et al. predictions [Liu 2013] were considered true)>

2) Predictions of 51 Samples from HapMap Projects

The high accuracy of HLAscan for the 1000-genome samples was verified, and predictions of HLAscan for 51 public HapMap samples were additionally performed in order to increase the reliability of HLAscan.

The samples used in this test were generated by Baylor College of Medicine (BCM) and Washington University Genome Sequencing Center (WUGSC) in 2013 and had verified HLA types [see Erlich2013, HLAreporter2015].

Predictions of HLAreporter were also performed for the same 51 samples as described above, and the results were used as comparisons.

Because of difficulty in HLA-typing due to characteristics such as the extreme levels of polymorphism and linkage disequilibrium of HLA regions, high-quality samples are necessary to increase accuracy.

The numbers of samples that passed the quality test presented in the HLA-reporter are 18, 18, 11, 45 and 46 in HLA-B, HLA-C, HLA-DRB1 and HLA-DQB1, respectively, which indicate the results of predictions of HLAscan for the samples.

(Description of Final Results for A, B and C)

Although the prediction results of [de Baker, 2006] are used as a gold standard for HapMap samples, [Rachel L Erlich 2011] found several mistyped cases through in-depth studies on class I regions, thereby providing more accurate HLA types.

When they are considered correct, the HLAscan and the HLAreporter all show 100% accuracy for HLA-A, HLA-B and HLA-C genes. As a level of 4-digits, the HLAscan has 100% accuracy, whereas the HLAreporter has accuracies of 80.5%, 83.3% and 95.5% for the three genes, respectively (see Table 2).

(Description of Final Results for DRB1 and DQB1)

When the results of [de Baker, 2006] for the Class II region, the HLAscan has accuracies of 96.6% and 95.6% at levels of 2-digits and 4-digits, respectively, for the HLA-DRB1 gene, and accuracies of 100% and 91.3% at levels of 2-digits and 4-digits, respectively.

The HLAreporter has accuracies of 97.8% and 95.6% for the HLA-DRB1 gene, and 98.9% and 89.1% for the HLA-DQB1 gene.

TABLE 2

| Methods | Genes | # of tested alleles | Phase | Ambiguity (4-digits) | Wrong (2-digits) | Wrong (4-digits) | Accuracy (2-digits) | Accuracy (4-digits) |
|---|---|---|---|---|---|---|---|---|
| HLA reporter | A | 36 | 5 | 7 | 0 | 0 | 100% | 80.5% |
|  | B | 36 | 7 | 3 | 0 | 2 | 100% | 83.3% |
|  | C | 22 | 4 | 0 | 0 | 1 | 100% | 95.5% |
| HLA scan | A | 36 | — | — | 0 | 0 | 100% | 100% |
|  | B | 36 | — | — | 0 | 0 | 100% | 100% |
|  | C | 22 | — | — | 0 | 0 | 100% | 100% |

<Table 2. HLA-A, HLA-B, and HLA-C genes in class I (10x = 100% and 20x ≥ 90%) (HLA-typing results [Rachel L Erlich2011])>

TABLE 3

| Methods | HLA Genes | # of tested alleles | Phase | Ambiguity (4-digits) | Wrong (2-digits) | Wrong (4-digits) | Accuracy (2-digits) | Accuracy (4-digits) |
|---|---|---|---|---|---|---|---|---|
| HLA reporter | DRB1 | 90 | 2 | 1 | 2 | 1 | 97.8% | 95.6% |
|  | DQB1 | 92 | 0 | 7 | 1 | 2 | 98.9% | 89.1% |
| HLA scan | DRB1 | 90 | — | — | 3 | 1 | 96.6% | 95.6% |
|  | DQB1 | 92 | — | — | 0 | 8 | 100% | 91.3% |

<Table 3. HLA-DRB1 and HLA-DQB1 genes in class II (10x ≥ 95%)>

[Analysis of Mistyped Allele]

When 12 mistyped alleles are collected, it can be seen that specific alleles are mistyped.

Referring to Table 4 below, the HLAscan shows three mistyped cases of 16:01 for 15:01, two mistyped cases of 06:09 for 06:05 and six mistyped cases of 02:02 for 02:01 (compared to gold standards), which occur repeatedly except for a mistyped case of 14:141 for 14:01, in all specific alleles. These are similar to the results reported in [PHLAT].

TABLE 4

<Mistyped alleles>

| Genes | Gold standard | | Predictions of HLA scan | | # of the cases |
|---|---|---|---|---|---|
| DRB1 | 11:04 | 14:01 | 11:04 | 14:141 | 1 |
|  | 15:01 | 15:01 | 15:01 | 16:01 | 3 |
| DRB1 | xx:yy | 06:05 | xx:yy | 06:09 | 2 |
|  | pp:qq | 02:01 | pp:qq | 02:02 | 6 |

As can be seen in FIG. 5, DRB1*02:01:01:01 and DRB1*02:02:01:01 alleles have 'T' and 'C', respectively, at position 162 of the exome region, indicating that only one sequence differs therebetween. The exome 2 region is identical therebetween.

FIG. 6 is a samtools tview showing that sequence reads of an NA11830 sample were actually mapped to DRB1*02:01:01:01 and DRB1*02:02:01:01.

Many sequence reads that support sequence 'C' at position 162 in exome 3 of DRB1*02:02:01:01 exist, while sequence sequences that support the corresponding sequence 'T' of DRB1*02: reads does not exist. Among 12 mistyped cases, 11 mistyped cases other than a case of DRB1*14:141 for DRB1*14:01 are similar to the above-described cases.

Results of Predictions for 5 Korean Samples

It was shown that the HLAscan had very high accuracy for 11 public 1000-genome samples and 51 HapMap samples. For clinical applications, high quality sequences compared to public data of 1000-genome and HapMap were generated from 5 Korean samples by use of the Invitrogen SeCore HLA-SBT kit, and were subjected to predictions using the HLAscan.

To verify the accuracy of the HLAscan, HLA typing was performed using a PCR-SBT (sequence based typing) method, and the results are compared.

Referring to Table 5 below, it can be seen that the predictions of HLAscan for the HLA-A, HLA-B, HLA-DRB1 of the 5 samples showed 100% concordance with the results of the PCR method. The HLAreporter showed four mistyping results despite the use of high-quality sequences.

TABLE 5

| Samples | Methods | HLA-A | | HLA-B | | HLA-DRB1 | |
|---|---|---|---|---|---|---|---|
| 77072421 | PCR-SBT | 02:06 | 02:10 | 40:02 | 55:02 | 04:05 | 11:01 |
| NS1512240004 | HLAreporter | 02:10 | 02:10 | 40:02:01 | 55:02:01 | 04:05:01 | 11:01:01 |
|  | HLAscan | 02:06:01G | 02:10 | 40:02:01 | 55:02:01G | 04:05:01 | 11:01:01 |
| 77072412 | PCR-SBT | 24:02 | 31:01 | 35:01 | 51:02 | 09:01 | 09:01 |
| NS1512240008 | HLAreporter | 24:82 | 31:01:02 | 35:42:02 | 51:02:02 | 09:01:02 | 09:01:02 |
|  | HLAscan | 24:02:01G | 31:01:13 | 35:01:01G | 51:02:01 | 09:01:02 | 09:01:02 |
| 77072374 | PCR-SBT | 02:01 | 33:03 | 15:01 | 44:03 | 09:01 | 13:02 |
| NS1512240012 | HLAreporter | 02:01:01 | 33:03:01 | 15:01:01 | 44:03:11 | 09:01:02 | 13:02:01 |
|  | HLAscan | 02:01:01G | 33:03:23 | 15:01:01G | 44:03:01 | 09:01:02 | 13:02:01 |
| 77072406 | PCR-SBT | 11:01 | 26:01 | 44:02 | 46:01 | 09:01 | 13:01 |
| NS1512240016 | HLAreporter | 11:01:01 | 26:01:01 | 44:02:01 | 46:01:01 | 09:01:02 | 13:01:01 |
|  | HLAscan | 11:01:01:01 | 26:01:01:01 | 44:02:01G | 46:01:01 | 09:01:02 | 13:01:01 |
| 77072287 | PCR-SBT | 02:01 | 02:06 | 13:01 | 40:02 | 08:02 | 12:02 |
| NS1512240020 | HLAreporter | 02:01:01 | 02:01:01 | 13:01:01 | 40:02:01 | 08:02:01 | 12:02:01 |
|  | HLAscan | 02:01:01G | 02:06:01G | 13:01:01 | 40:02:01 | 08:02:01 | 12:02:01 |

<Table 5. Our results>

The scope of the present invention is not limited to the above-described embodiments, but is defined by the appended claims, and those skilled in the art will appreciate that various modifications and alterations are possible without departing from the scope of the present invention as defined in the appended claims.

INDUSTRIAL APPLICABILITY

The present invention relates to human haplotyping which has increased accuracy and efficiency in detecting genotypes for identifying human genetic traits through a computerized system. According to the present invention, while haplotyping is performed using short sequence reads based on an alignment based approach, the efficiency of selection of candidate alleles can be increased. In addition, false alleles caused by phase issues can be detected by use of a unique read algorithm.

sequence reads as a tiling array pattern, wherein determination of the distribution of the aligned sequence reads comprises converting the distribution of the aligned reads into a score, and determining that the alleles are false alleles, when the score is lower than a threshold value; and an allele determination step of selecting a final allele from among the candidate alleles, wherein the score is calculated by the following equation:

$$score = \sum_{j=1}^{m} \left( \frac{|noreadj|}{c} \right)^4$$

---

---

The invention claimed is:

1. A human haplotyping method comprising:
    a sequence read collection step of collecting a sequence of a gene to be analyzed;
    a sequence read alignment step of matching and aligning reads of the collected sequence to a reference stored in a database, comprising steps of aligning the sequence leads to the reference stored in the database and filtering the aligned sequence reads depending on an absolute value of matching with the reference alleles;
    an allele selection step of selecting candidate alleles from among alleles of the reference by selecting the candidate alleles depending on a distribution of the aligned sequence reads as a tiling array pattern, wherein determination of the distribution of the aligned sequence reads comprises converting the distribution of the aligned reads into a score, and determining that the alleles are false alleles, when the score is lower than a threshold value; and
    an allele determination step of selecting a final allele from among the candidate alleles,
    wherein the score is calculated by the following equation:

$$score = \sum_{j=1}^{m} \left( \frac{|noreadj|}{c} \right)^4$$

wherein m is a value determined depending on the length of the alleles; C is a constant; and noread is a constant determined for a region to which the sequence reads are not aligned.

2. The human haplotyping method of claim 1, wherein the sequence read collection step comprises a step of selecting and collecting sequence reads of a specific region.

3. The human haplotyping method of claim 2, wherein the specific region is a region selected from human gene regions.

4. The human haplotyping method of claim 3, wherein the database is a haplotype DB for human genes.

5. The human haplotyping method of claim 2, wherein the specific region is an HLA gene region as an example.

6. The human haplotyping method of claim 5, wherein the database is an IMGT/HLA DB as an example.

7. The human haplotyping method of claim 1, wherein the allele gene determination step is performed by a unique read algorithm, in which the unique read algorithm is configured such that when 4 or more candidate alleles are present on the reference, the algorithm excludes candidate alleles other than alleles, which 100% match with the sequence reads, from the four or more candidate alleles.

8. The human haplotyping method of claim 1, wherein the allele determination step is performed by a unique read algorithm, in which the unique read algorithm is configured such that when 3 or less candidate alleles are present on the reference, the algorithm counts the number of unique reads which are sequence reads aligned to only any one of the candidate alleles, and the algorithm selects two final candidate alleles depending on the number of the unique reads.

9. The human haplotyping method of claim 8, wherein the unique read algorithm is configured such that when the two final candidate alleles include different unique reads, the algorithm determines the alleles as heterozygous alleles.

10. The human haplotyping method of claim 8, wherein the unique read algorithm is configured such that when any one of the two final candidate alleles includes unique reads, the algorithm determines the alleles as homozygous alleles.

11. A human haplotyping system configured to:
match and align sequence reads, collected from a gene to be analyzed, to reference alleles stored in a database;
select candidate alleles from among the reference alleles by selecting the candidate alleles depending on a distribution of the aligned sequence reads as a tiling array pattern, wherein determination of the distribution of the aligned sequence reads comprises converting the distribution of the aligned reads into a score, and determining that the alleles are false alleles, when the score is lower than a threshold value; and
select two final alleles from among the candidate alleles, wherein the aligning of the sequence reads is performed by aligning the sequence reads to the reference stored in the database, and then filtering the aligned sequence reads depending on an absolute value of matching with the reference alleles, and wherein the score is calculated by the following equation:

$$\text{score} = \sum_{j=1}^{m}\left(\frac{|noreadj|}{c}\right)^4$$

wherein m is a value determined depending on the length of the alleles; C is a constant; and noread is a constant determined for a region to which the sequence reads are not aligned.

12. The human haplotyping system of claim 11, wherein the sequence read collection comprises selecting and collecting sequence reads of a specific region.

13. The human haplotyping system of claim 12, wherein the specific region is an HLA gene region as an example.

14. The human haplotyping system of claim 11, wherein the selection of the final allele is performed by a unique read algorithm, in which the unique read algorithm is configured such that when 4 or more candidate alleles are present on the reference, the algorithm excludes candidate alleles other than alleles, which 100% match with the sequence reads, from the four or more candidate alleles.

15. The human haplotyping system of claim 11, wherein the selection of the final allele is performed by a unique read algorithm, in which the unique read algorithm is configured such that when 3 or less candidate alleles are present on the reference, the algorithm counts the number of unique reads which are sequence reads aligned to only any one of the candidate alleles, and the algorithm selects two final candidate alleles depending on the number of the unique reads.

16. The human haplotyping system of claim 15, wherein the unique read algorithm is configured such that when the two final candidate alleles include different unique reads, the algorithm determines the alleles as heterozygous alleles.

17. The human haplotyping system of claim 15, wherein the unique read algorithm is configured such that when any one of the two final candidate alleles includes unique reads, the algorithm determines the alleles as homozygous alleles.

* * * * *

SEQUENCE LISTING

<160> NUMBER OF SEQ ID NOS: 2

<210> SEQ ID NO 1
<211> LENGTH: 282
<212> TYPE: DNA
<213> ORGANISM: Homo sapiens

<400> SEQUENCE: 1

```
gccactccac ggtgatgggg ctctggaggc tggggtgctc cacgtggcag gtgtagacgt      60
ctccacgctg gggagtcatt tccagcatca ccaggatctg gaaggtccag tcaccattcc     120
taataagggg ggtggacaca acgccagctg tctcctcctg gtcattccga aaccaccgga    180
ctttgatctg ggctggatag aaatctgtca ccgagcagac cagcaggttg tggtggttga    240
gggcctctgt cctggatggg gagatggtca ctgtgggctc ca                       282
```

<210> SEQ ID NO 2
<211> LENGTH: 281
<212> TYPE: DNA
<213> ORGANISM: Homo sapiens

<400> SEQUENCE: 2

```
gccactccac ggtgatgggg ctctggaggc tggggtgctc cacgtggcag gtgtagacgt      60
ctccacgctg gggagtcatt tccagcatca ccaggatctg gaaggtccag tcaccattcc     120
taataagggg ggtggacaca acgccagctg tctcctcctg gccattccga aaccaccgga    180
ctttgatctg ggctggatag aaatctgtca cgagcagacc agcaggttgt ggtggttgag    240
ggcctctgtc ctggatgggg agatggtcac tgtgggctcc a                        281
```